United States Patent
Krockenberger et al.

(10) Patent No.: US 8,906,309 B2
(45) Date of Patent: Dec. 9, 2014

(54) METHOD FOR DISCRIMINATING RED BLOOD CELLS FROM WHITE BLOOD CELLS BY USING FORWARD SCATTERING FROM A LASER IN AN AUTOMATED HEMATOLOGY ANALYZER

(75) Inventors: Martin Krockenberger, Los Gatos, CA (US); Jiong Wu, Los Gatos, CA (US); Bodo Roemer, Saulheim (DE); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 728 days.

(21) Appl. No.: 12/767,611

(22) Filed: Apr. 26, 2010

(65) Prior Publication Data

US 2010/0273168 A1    Oct. 28, 2010

Related U.S. Application Data

(60) Provisional application No. 61/172,999, filed on Apr. 27, 2009.

(51) Int. Cl.
| | | |
|---|---|---|
| G01N 33/00 | (2006.01) | |
| G01N 31/00 | (2006.01) | |
| G01N 15/00 | (2006.01) | |
| G01N 15/14 | (2006.01) | |
| G01N 33/49 | (2006.01) | |

(52) U.S. Cl.
CPC ........ *G01N 15/00* (2013.01); *G01N 2015/0076* (2013.01); *G01N 2015/008* (2013.01); *G01N 2015/0084* (2013.01); *G01N 2015/1486* (2013.01); *G01N 2015/0073* (2013.01); *G01N 33/49* (2013.01)
USPC .................. 422/73; 422/50; 422/400; 436/10

(58) Field of Classification Search
CPC .......... G01N 15/1434; G01N 15/1459; G01N 2021/0346; G01N 2021/6493; G01N 21/6428; G01N 21/645; G01N 15/00; G01N 2015/0073; G01N 2015/0076; G01N 2015/008; G01N 2015/0084; G01N 2015/1486; G01N 33/49
USPC ............................... 422/50, 73, 400; 436/10
See application file for complete search history.

(56) References Cited

U.S. PATENT DOCUMENTS

| | | |
|---|---|---|
| 4,284,355 A | 8/1981 | Hansen et al. |
| 4,735,504 A | 4/1988 | Tycko |

(Continued)

OTHER PUBLICATIONS

CELL-DYN Sapphire™. Abbott Diagnostics Products [online]. Abbott Laboratories, 2008 [retrieved on Nov. 25, 2007] Retrieved from the Internet: <URL: http://www.abbottdiagnostics.com/Products/Instruments_by_Platform/default.cfm? system=CELL-DYN &suffix=sapphire>.

(Continued)

*Primary Examiner* — Dean Kwak
(74) *Attorney, Agent, or Firm* — Edward J. Baba; Benjamin C. Pelletier; Bozicevic, Field & Francis LLP

(57) ABSTRACT

A method for identifying, analyzing, and quantifying the cellular components of whole blood by use of an automated hematology analyzer and the detection of the light scattered, absorbed, and fluorescently emitted by each cell. More particularly, the aforementioned method involves identifying, analyzing, and quantifying the cellular components of whole blood by use of a light source having a wavelength ranging from about 400 nm to about 450 nm and multiple in-flow optical measurements and staining without the need for lysing red blood cells.

16 Claims, 8 Drawing Sheets

(56) References Cited

U.S. PATENT DOCUMENTS

| | | | |
|---|---|---|---|
| 4,882,284 A | 11/1989 | Kirchanski et al. | |
| 5,017,497 A | 5/1991 | Gerard de Grooth et al. | |
| 5,138,181 A | 8/1992 | Lefevre et al. | |
| 5,194,909 A | 3/1993 | Tycko | |
| 5,284,771 A | 2/1994 | Fan et al. | |
| 5,350,695 A | 9/1994 | Colella et al. | |
| 5,360,739 A | 11/1994 | Fan et al. | |
| 5,438,003 A | 8/1995 | Colella et al. | |
| 5,516,695 A | 5/1996 | Kim et al. | |
| 5,559,037 A | 9/1996 | Kim et al. | |
| 5,601,234 A * | 2/1997 | Larue | 239/1 |
| 5,631,165 A | 5/1997 | Chupp et al. | |
| 5,648,225 A | 7/1997 | Kim et al. | |
| 5,812,419 A | 9/1998 | Chupp et al. | |
| 5,939,326 A * | 8/1999 | Chupp et al. | 436/43 |
| 6,025,201 A | 2/2000 | Zelmanovic et al. | |
| 6,114,173 A | 9/2000 | Zelmanovic et al. | |
| 6,524,581 B1 | 2/2003 | Adamis | |
| 6,524,858 B1 | 2/2003 | Zelmanovic et al. | |
| 6,579,685 B1 | 6/2003 | Russell et al. | |
| 6,618,143 B2 | 9/2003 | Roche et al. | |
| 6,623,972 B2 | 9/2003 | Malin et al. | |
| 6,670,321 B1 | 12/2003 | Adamis | |
| 7,061,595 B2 | 6/2006 | Cabuz et al. | |
| 7,361,512 B2 | 4/2008 | Qian et al. | |
| 7,397,232 B2 | 7/2008 | Hu et al. | |
| 7,471,394 B2 | 12/2008 | Padmanabhan et al. | |
| 7,553,453 B2 | 6/2009 | Gu et al. | |
| 7,625,712 B2 | 12/2009 | Paul et al. | |
| 7,630,063 B2 | 12/2009 | Padmanabhan et al. | |
| 7,674,598 B2 | 3/2010 | Paul et al. | |
| 2003/0025896 A1 | 2/2003 | Oever et al. | |
| 2003/0129090 A1* | 7/2003 | Farrell | 422/68.1 |
| 2003/0143117 A1 | 7/2003 | Nagai et al. | |
| 2005/0219527 A1 | 10/2005 | Ikeuchi et al. | |
| 2007/0190525 A1 | 8/2007 | Gu et al. | |
| 2008/0153170 A1 | 6/2008 | Garrett et al. | |
| 2008/0158561 A1 | 7/2008 | Vacca et al. | |
| 2008/0254543 A1 | 10/2008 | Ryan | |
| 2008/0268494 A1 | 10/2008 | Linssen | |
| 2009/0042310 A1* | 2/2009 | Ward et al. | 436/154 |
| 2009/0142765 A1 | 6/2009 | Vacca et al. | |

OTHER PUBLICATIONS

CELL-DYN Ruby. Abbott Diagnostics Products [online]. Abbott Laboratories, 2010 [retrieved on Jul. 30, 2010] Retrieved from the Internet: <URL: http:/abbottdiagnostics.com/Products/Instruments__by__Platform/default.cfm?system=cell-dyn&suffix=ruby>.

Forgy, Cluster Analysis of Multivariate Data: Efficiency vs. Interpretability of Classifications, Biometrics, 1965, pp. 768-769, vol. 21.

Hartigan and Wong, Algorithm AS 136: A K-Means Clustering Algorithm, Journal of the Royal Statistical Society, Series C (Applied Statistics), 1979, pp. 100-108, vol. 28, No. 1.

Lloyd, Least Squares Quantization in PCM, IEEE Transactions on Information Theory, 1982, pp. 129-137, vol. IT-28, No. 2.

MacQueen, Some Methods for Classification and Analysis of Multivariate Observations, 1967, pp. 281-297, University of California.

Thomas, et al., Biochemical Markers and Hematologic Indices in the Diagnosis of Functional Iron Deficiency, Clinical Chemistry, 2002, pp. 1066-1076, vol. 48:7.

Wlodkowic, et al., SYTO probes in the cytometry of tumor cell death. Cytometry, vol. 73A, Issue 6, pp. 496-507 [online]. 2008 [retrieved on Jul. 22, 2010]. Retrieved from the Internet: <URL: http://www3.interscience.wiley.com/cgi-bin/fulltext/117908525/main.html,ftx__abs>.

Wlodkowic, et al., Multiparameter detection of apoptosis using red-excitable SYTO probes, Cytometry, vol. 73A, Issue 6, pp. 563-569 [online]. 2008 [retrieved on Jul. 22, 2010]. Retrieved from the Internet: <URL: http://www3.interscience.wiley.com/cgi-bin/fulltext/118824426/main.html,ftx__abs>.

The PCT International Search Report, PCT/US10/32429, Date of mailing Aug. 20, 2010.

* cited by examiner

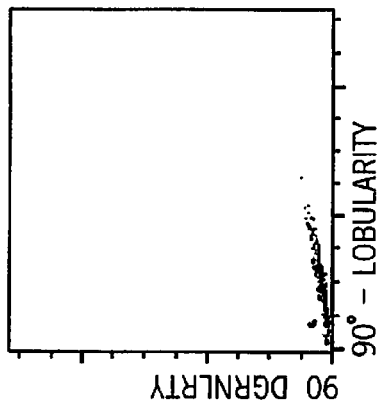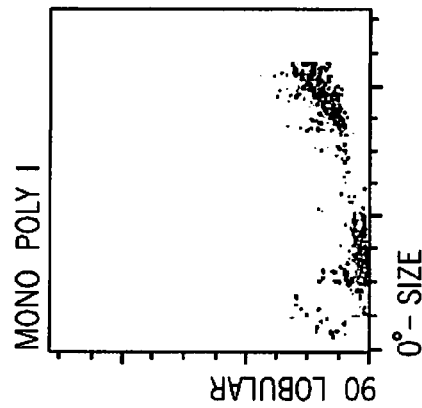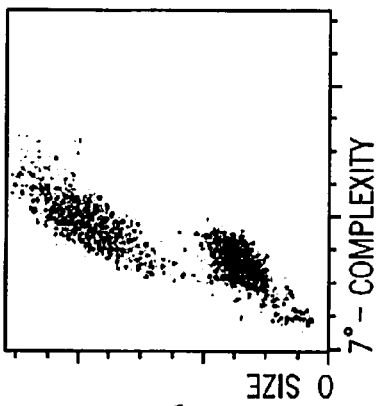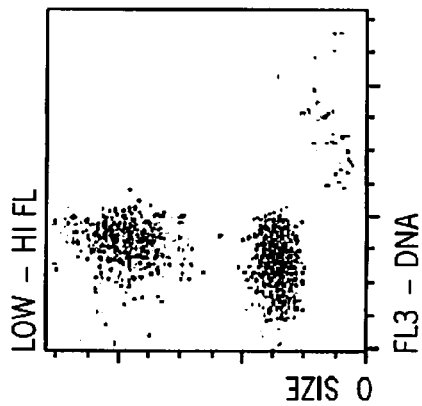

METHOD FOR DISCRIMINATING RED BLOOD CELLS FROM WHITE BLOOD CELLS BY USING FORWARD SCATTERING FROM A LASER IN AN AUTOMATED HEMATOLOGY ANALYZER

BACKGROUND OF THE INVENTION

1. Field of the Invention

Certain embodiments of this invention relate to a method for identifying, analyzing, and quantifying the cellular components of whole blood by means of an automated hematology analyzer and the detection of the light scattered and absorbed by each cell. More particularly, the aforementioned method may involve identifying, analyzing, and quantifying the cellular components of whole blood by means of multiple in-flow optical measurements using a single dilution of sample without the need for lysing red blood cells.

2. Discussion of the Art

Some automated hematology analyzers are equipped with an optical bench that can measure multiple in-flow optical measurements, such as light scattering, extinction, and fluorescence, as described in U.S. Pat. Nos. 5,631,165 and 5,939,326, both of which are incorporated herein by reference. Furthermore, U.S. Pat. Nos. 5,516,695 and 5,648,225, both of which are incorporated herein by reference, describe a reagent suitable for lysing red blood cells and staining nuclear DNA of membrane-lysed erythroblasts to discriminate white blood cells from erythroblasts. Membrane-lysed erythroblasts are erythroblasts wherein the membrane thereof has undergone lysis. U.S. Pat. No. 5,559,037, incorporated herein by reference, describes the simultaneous detection of erythroblasts and white blood cell differential by means of a triple triggering circuitry, which is used to eliminate noise signals from cell debris, such as, for example, membranes of lysed red blood cells, which are located below the lymphocyte cluster along the Axial Light Loss (ALL) axis of a cytogram. However, the use of lysing agents to lyse red blood cells brings about certain difficulties and complications in the detection of white blood cells. The lysing agent may be insufficiently strong, thereby resulting in red blood cells being counted as white blood cells. Alternatively, the lysing agent may be excessively strong, thereby resulting in artificially low counts of white blood cells. Different samples require lysing agents of different strengths in order to obtain accurate counts of white blood cells; accordingly, all hematology analyzers currently in use sometimes yield incorrect counts of white blood cells, listing various kinds of lysis-resistant red blood cells as interfering substances.

In hematological assays aimed at determining parameters from human whole blood, there are two physiological factors that present obstacles to simple, rapid, and accurate determination of cell counts. One factor is that, in typical fresh peripheral human whole blood, there are about 1,000 red blood cells and about 50 platelets for each white blood cell. The other factor is that, while platelets are typically sufficiently smaller than any other cell type to allow discrimination based on size, and most white blood cells are sufficiently larger than either red blood cells or platelets to again allow discrimination based on size, two cell species in particular—red blood cells and lymphocytes, a subtype of white blood cells—typically overlap in size distribution (as well as in their scattering signatures) to a sufficient degree to make discrimination based on size prone to gross error. Therefore, when determining red blood cells mainly by size discrimination, the asymmetry in concentration can work in one's favor, since the occasional white blood cell misclassified as a red blood cell will not, generally, affect the overall accuracy of the measured concentration of red blood cells to any appreciable degree; however, the converse is not true, and any unaccounted-for interference from red blood cells in determining the concentration of lymphocytes (and, by extension, the overall concentration of white blood cells) can yield very inaccurate results.

Consequently, methods have been developed in the prior art to handle this large asymmetry and size overlap and still provide useful results in an acceptable time frame. One standard method employed in the prior art has been to separate the blood sample to be analyzed into at least two aliquots, one destined for red blood cell and platelet analysis, and one for white blood cell analysis. The aliquot destined for white blood cell analysis is mixed with a reagent solution containing a lysing reagent that attacks the membranes of the red blood cells preferentially, or faster than it attacks those of the white blood cells. Partially on account of their loss of hemoglobin through the compromised membrane, and partially on account of their attendant reduction in size, the resulting lysed red blood cells become distinguishable from lymphocytes based on their respective scattering signatures. Another method employed in the prior art involves using nucleic acid dyes to provide a fluorescent distinction between the red blood cells and the white blood cells. White blood cells contain a nucleus containing DNA. When these white blood cells are identified via a fluorescent label, they can be distinguished from mature red blood cells, whose nuclei have been expelled in the maturation process.

Both of these methods have drawbacks. First of all, the lysing reagent used to dissolve the red blood cells can attack the white blood cells as well, reducing their integrity and eventually dissolving them, too. This is particularly a problem with white blood cells that are already fragile in the first place, due to some pathological condition (such, as, for example, chronic lymphocytic leukemia). At the other end are types of red blood cells (such as, for example, those found in neonates, and in patients with thalassemia, sickle-cell anemia, and liver disease) which are naturally resistant to lysis, and which therefore tend to persist as interferents in white blood cell assays involving lysis. In order to reduce the likelihood of either degradation of white blood cells or interference from unlysed red blood cells (either of which would jeopardize the accuracy of the overall white blood cell concentration measurement), a careful combination of concentration of lysing agent, temperature control, and incubation time can be used. In some cases, the user is offered several test options with different lysing conditions, thereby allowing the user to tailor the assay to the subject patient sample. This tailoring, however, is a complex solution, which additionally either requires prior knowledge of the state of the patient, or must be used as a reflex test following a standard complete blood count (CBC).

Regarding the fluorescence-based approach at discriminating between red blood cells and lymphocytes, the main obstacle is the measurement rate. When white blood cells are measured at the same time as red blood cells and platelets, the presence of red blood cells sets an upper limit to the concentration that can be sent through the analyzer without incurring in coincidences at an unacceptably high rate; the dilution ratio used to achieve such concentration, in turn, limits the rate at which white blood cell events are being counted; and in order to obtain the counting precision expected of the analyzer, this relatively low rate of white blood cell event acquisition, in turn, forces long acquisition times. For example, the concept of measuring all of the components of blood from a single sample in one pass was disclosed in U.S. Pat. No. 6,524,858.

As noted in that disclosure, the method would be capable of a cycle time of 88 seconds, or about 41 CBC/hr. This throughput is far lower than that achievable by most automated hematology analyzers commercially available today, severely limiting its commercial usefulness. The CELL-DYN® Sapphire® hematology analyzer, as another example, presently offers a test selection (requiring yet another aliquot of sample in addition to those used in the red blood cell/platelet assay and in the white blood cell assay) employing a nucleic-acid dye capable of differentiating between intact (unlysed) red blood cells and lymphocytes. This test selection uses the dye primarily to differentiate between mature red blood cells and reticulocytes, a subset of immature red blood cells that retain dye-absorbing RNA in the cytoplasm. While it would technically be possible to count the white blood cells using this same assay, as they are sufficiently differentiated by fluorescence from either red blood cells or reticulocytes to obtain the desired accuracy, the relatively low concentration of white blood cells in the dilution used makes it an impractical option to achieve the required statistical precision. Such a scheme would require an acquisition time of approximately 75 seconds, limiting throughput to only 48 CBC/hr. Accordingly, although this approach is theoretically feasible, a much higher throughput would be required in order for this approach to become practical commercially.

A single-dilution approach presents many potentially attractive benefits. One of them is the elimination of multiple aliquots. This feature drastically simplifies the fluidic architecture of the system, since it requires only a single container (instead of two or more) in which to mix the blood sample and the reagent solution, and only a single system (such as, for example, a precision metering syringe and associated driver motor and control electronics) for measuring and delivering the reagent solution to the mixing container. It also affords an attendant reduction in the number of valves, the number of valve actuators, the number of individual segments of tubing, and the number and quantity of reagents necessary to implement the desired assay. Another benefit is the elimination of the process of lysing red blood cells. This feature reduces drastically the uncertainties associated with lysis-resistant red blood cells and with lysis-prone lymphocytes; it eliminates the need for the time-consuming and sensitive lysis incubation period; and, additionally, it eliminates a significant portion of the software dedicated to operate the analyzer, as previously separate test selections are combined in a single procedure. Another benefit accrues from the overall reduction in complexity of the analyzer due to the individual changes just described.

There are additional potential attendant reductions in complexity. Hematology analyzers designed for high throughput may also generally include additional transducers in addition to the flow cytometer subassembly incorporated therein, such as, for example, one or more impedance transducers to count, size, and identify some subpopulations of blood cells, and a colorimetric transducer to determine the hemoglobin-related parameters of blood. A single-dilution approach could eliminate the need for additional impedance transducers, for a colorimetric transducer, or for both impedance transducers and colorimetric transducers, if the analyzer were capable of achieving sufficient speed, precision, and accuracy in measurement to render these deletions practical. Because the colorimetric transducer for bulk measurement of hemoglobin requires the use of a strong lysing agent to dissolve the membranes of the red blood cells (the lysing agent typically being in addition to the milder lysing agent used in the white blood cell assays), elimination of the colorimetric transducer may also eliminate the need for an additional on-board strong lysing agent in addition to that used in the flow cytometer subassembly. The reduction in complexity, whether from (a) simply replacing the flow cytometer subassembly of the prior art with a single-dilution subassembly while maintaining a separate colorimetric transducer or an impedance transducer or both, or from (b) additionally incorporating all the functions of impedance transducers and colorimetric transducers into a single-dilution analyzer, may result in a substantial improvement in the reliability of the instrument, because the number of parts subject to failure would be reduced, and because the number of components generating heat (which can reduce the lifetime of some components) would be reduced. This potential improvement in reliability would likewise provide a major improvement in the instrument's service profile, with less maintenance required, fewer service calls required, and a lower cost for those calls that do occur, on account of the increased serviceability of a simplified instrument architecture, i.e., an instrument having fewer components. Beside the reliability improvements, a simplification in the instrument architecture would also reduce its cost, on account of both a reduced part count and simplified assembly and testing activities during its manufacture.

All of these benefits, however, are overshadowed in the prior art by the low throughput of the disclosed method. In other words, the single-dilution feature disclosed in the prior art is only one of the enabling elements of a superior analyzer. It would be desirable to enhance the single-dilution approach with a high measurement rate in order to also provide the throughput performance commonly expected of commercial hematology analyzers, and typically expected of analyzers designed for high-volume environments.

Therefore, it would be desirable to develop a method for identifying, analyzing, and quantifying the cellular components of whole blood by means of multiple in-flow optical measurements without the need for lysing red blood cells.

SUMMARY OF THE INVENTION

A method and a hematology analyzer for performing the method are provided. In certain embodiments, the hematology analyzer comprises: (a) a flow cell through which a whole blood sample is introduced at a high rate or at a low rate; (b) a laser having a wavelength in the range of from about 400 nm to about 450 nm for directing light to the flow cell; (c) a plurality of detectors for detecting the interaction of light with cells on a plurality of optical measurement channels; and (d) a data analysis workstation comprising: i. programming to differentiate and count white blood cells in the sample using multiple in-flow optical measurements obtained from a first portion of the sample that has been introduced into the flow cell at a high rate; ii. programming to differentiate and count red blood cells and platelets in the sample using multiple in-flow optical measurements obtained from a second portion of the sample that has been introduced into the flow cell at a low rate. In certain cases the workstation may further comprise: iii. programming to measure hemoglobin-related parameters on a cell-by-cell basis, as discussed in greater detail below. In one aspect, the method comprises the steps of: (a) providing an automated hematology analyzer capable of measuring light extinction, light scattering, and fluorescence, the automated hematology analyzer being equipped with a laser having a wavelength in the range of from about 400 nm to about 450 nm; (b) providing a diluent for diluting a sample of blood which, in certain cases, contains a sphering agent; (c) providing a sample of whole blood; (d) mixing the diluent and the sample of whole blood; (e) differentiating and counting white blood cells by means of multiple in-flow optical measurements with a high rate of sample introduction; (f) differentiating and counting red blood cells and platelets by means of multiple in-flow optical measurements with a low rate of sample introduction; and (g) measuring the concentration of hemoglobin of the whole blood sample by measuring the concentration of hemoglobin in each individual red blood cell by means of multiple in-flow optical measurements and using the red blood cell counts from step (f) to determine the concentration of red blood cells in the whole blood sample. In order to measure the concentration of erythroblast cells, the method comprises the additional steps of (a) staining erythroblast nuclei with a nuclear stain; (b) detecting erythroblasts by means of at least one of extinction, light scattering, and fluorescence from the nuclear stain; and (c) differentiating and counting the erythroblast cells by algorithms that analyze the separation of erythroblasts from other cell populations.

In order to measure the percentage of reticulocytes in the entire population of red blood cells, the method comprises the additional steps of (a) staining reticulocytes with an RNA stain; (b) detecting reticulocytes by means of at least one of extinction, light scattering, and fluorescence; and (c) differentiating reticulocytes and quantifying the reticulocyte percentage of red blood cells in the sample by algorithms that analyze the distribution of fluorescent signals in the red blood cell population.

The method described herein can further include the steps of (a) storing data for the analysis of the sample of whole blood, (b) reporting results for the analysis of the sample of whole blood, and (c) analyzing the sample of whole blood by at least one algorithm to count and differentiate white blood cells, erythrocytes, platelets, erythroblasts, and reticulocytes.

In one embodiment, the sample of blood is analyzed without any manual preparation (save homogenization of the sample in the sample collection tube by repeated inversions) in the Open Mode of the hematology analyzer. The samples prepared for onboard analysis using the diluent/sheath reagent are passed through the electro-optical flow-cytometry system described herein, whereupon the electronic logic of the system and the algorithm(s) of the system differentiate each cell population based on volume of the cells, refractive index of the cells, fluorescence intensity of the cells, presence and conformation of any nucleus inside the cells, presence and quantity of any cytoplasmic granules inside the cells, and the location and pattern of each cluster of cells in cytograms constructed from combinations of two or more of the optical measurements, or in histograms constructed from projections of the optical measurements along a chosen axis. As would be understood, when taking measurements at a high rate of flow, not all of the cells may be in single file. At a high rate of flow, the white blood cells (WBCs) may appear to be strung on in single file with good separation between individual cells, and the red blood cells (RBCs) may be frequently coincident with the WBCs. At a high flow rate, the IAS trigger allows the analyzer to ignore the RBCs. At lower flow rates, the RBCs should generally be in single file so they can be counted. The intermediate angle scattering (IAS) trigger qualifies signals from white blood cells. To be qualified as a valid white blood cell signal, i.e., a signal generated by a white blood cell, the amplitude of the signal must be above the intermediate angle scattering (IAS) trigger threshold; the algorithm(s) of the system carry out the function of differentiating the sub-populations of the white blood cells by using the intensity of the signals from a plurality of optical detectors, and the shape and the number of clusters.

The use of a laser having a wavelength ranging from about 400 nm to about 450 nm aids in the separation of red blood cells from white blood cells. The use of the aforementioned laser enables the hematology analyzer to function without the need for a lysing agent for red blood cells in order obtain an accurate count of white blood cells.

In one embodiment, the analyzer uses one single dilution of whole blood to count all of the cells in the sample. This count is achieved by using two different sample introduction rates for the diluted blood into the flow cell. The white blood cell count uses a sufficiently high sample introduction rate and an intermediate angle scattering (IAS) trigger in order to exclude platelets and red blood cells. The overall sample introduction rate for counting red blood cells and platelets is lower than the overall sample introduction rate used for counting white blood cells. This technique allows a sufficient number of white blood cell events to be collected in less than 40 seconds of counting time. Introduction of the diluted sample into the flow cell can be carried out by injection. The actual rates of sample introduction can be determined by one of ordinary skill in the art without undue experimentation. For example, in certain embodiments a low rate of sample introduction may be in the range of about 1,000-50,000 cells per second (for samples with typical concentrations found in normal adult blood); while in certain embodiments a high rate of sample introduction may be in the range of about 50,001-300,000 cells per second (for samples with typical concentrations found in normal adult blood).

In addition to the foregoing embodiments, the apparatus and method of this invention may employ elements representing a reduction in the number of corresponding elements conventionally used in current hematology analyzers and flow cytometers. These elements are: (a) a reagent system, free of lysing agent, that includes: i. a diluent and ii. a RNA- and DNA-staining fluorescent dye, or a combination of two different dyes that preferentially bind, respectively, to RNA and DNA; (b) a sample aspiration assembly capable of delivering a portion of a sample; (c) a single container for holding such portion and for mixing of such portion with the reagent solution; (d) one or more subsystems for metering and delivery of the appropriate amount of reagents into the sample aliquot container; (e) a single subsystem for staging the resulting solution of sample aliquot and reagent to the optical flow cell; (f) fluidic components necessary for rinsing the sample path and for waste disposal. In certain cases, the diluent can contain sphering agent, which, as described below, can be used in the detection of RBCs. As would be apparent, the diluent and the dye can be stored separately from one another and, in certain cases, can be combined with one another before use.

In one embodiment, the analyzer contains a colorimetric transducer for bulk detection and quantification of hemoglobin, appropriate fluidics, and appropriate electronics necessary to support the hemoglobin assay performed on such a transducer. In another embodiment, the analyzer does not possess a separate colorimetric transducer for the bulk measurement of hemoglobin (thereby eliminating the supporting fluidics and supporting electronics), having incorporated the hemoglobin-quantification function of such a transducer into the function of the flow cell in which is performed a single-dilution assay free of a lysing agent.

Also provided is a method of identifying and counting reticulocytes and nucleated red blood cells in a sample of blood. In certain embodiments, this method comprises: (a) providing an automated hematology analyzer equipped with a laser having a wavelength in the range of from about 400 nm to about 450 nm; (b) mixing a diluent comprising a fluorescent dye, e.g., from the SYTO family with a sample of whole blood, thereby staining reticulocytes and nucleated red blood cells in the sample with the fluorescent dye; and (c) detecting the reticulocytes and nucleated red blood cells in the sample by detecting fluorescence emitted by the fluorescent dye using the automated hematology analyzer. In certain cases, the blood sample can be introduced into the flow cell of the analyzer at a high rate, and at a low rate, as described below.

BRIEF DESCRIPTION OF THE DRAWINGS

FIGS. 6A, 6B, 6C, and 6D are cytograms illustrating the same sample as in FIGS. 5A, 5B, 5C, 5D and presenting a lymphocyte percentage of 48%. The cytograms were generated by a CELL-DYN® Sapphire® hematology analyzer using a conventional lysing agent of high lytic strength. The wavelength of the laser, 488 nm, was not in the range described herein (i.e., 400 nm to 450 nm).

DETAILED DESCRIPTION

Figure 1:
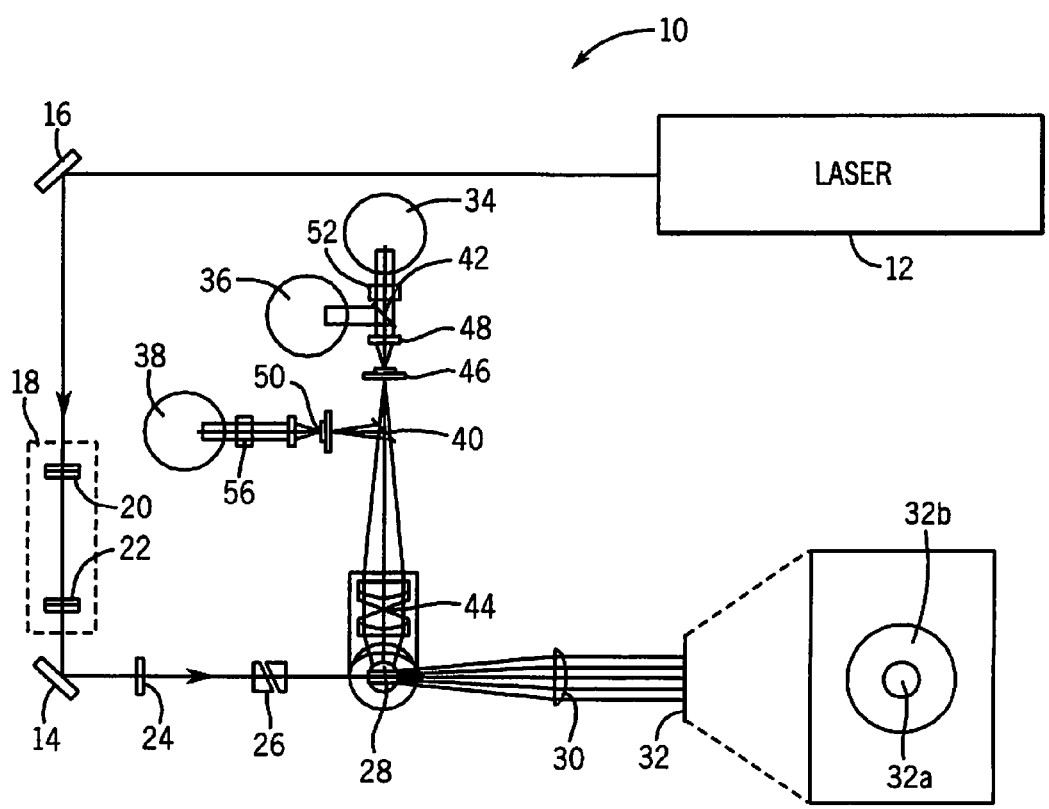
FIG. 1 is a schematic diagram illustrating the illumination and detection optics of an apparatus suitable for generating signals from cells on multiple detection channels for differential analysis.

As used herein, the expressions "axial light loss" and "ALL" refer to the measurement of the total light lost from the laser beam when a particle passes through the beam, and typically measured with a detector subtending a range of angles (measured from the cell or particle under study) from 0° (the optical axis of the system) to about 1°. This parameter relates to measurement of light extinction, which comprises light lost through scattering as well as absorption; in the absence of absorption, it is a measurement that correlates broadly with the size of cells or particles passing through the optical detection system.

As used herein, the expressions "small angle scattering" and "SAS" refer to the measurement of forward light scattering at small angles from about 1° to about 3°. For certain laser light wavelengths, e.g., for a wavelength of 633 nm, this parameter relates to measurement of the size of cells. For certain other laser light wavelengths, e.g., for a wavelength of 405 nm, this parameter relates to measurement of the refractive index of cells, which in turn is a measure of cytoplasmic content, such as, e.g., hemoglobin.

As used herein, the expressions "intermediate angle scattering" and "IAS" refer to the measurement of forward light scattering at intermediate angles from about 3° to about 10°. This parameter relates broadly to measurement of the complexity of a cell. As used herein, the term "complexity" refers to the composition of a cell. Some cells have mitochondria, ribosomes, and a nucleus, while other cells lack one or more of the foregoing components. The measured intensity of IAS depends to some degree on the heterogeneity of the contents of a cell (or particle) passing through the illumination beam of a cytometer. The intensity of IAS signals can be thought of as a measure of the complexity of the contents of the cell, i.e., the presence of organelles, such as, for example, nuclei, vacuoles, mitochondria, etc. For certain laser light wavelengths, the intensity of IAS signals additionally carries information on the average refractive index of cells.

As used herein, the expressions "polarized side scattering" and "PSS" refer to polarized (i.e., polarization-maintaining) light scattering into a cone centered around the angle of 90° and having an angular half-width of between around 10° and around 75°. This parameter relates broadly to measurement of lobularity. The nuclei of cells have various shapes that may result in one to five lobules, inclusive. A representative example of a cell with multi-lobed nucleus is a segmented neutrophil; higher lobularity tends to correlate with increased PSS signals.

As used herein, the expressions "depolarized side scatter" and "DSS" refer to depolarized (i.e., polarization-rotating) light scattering into a cone centered around the angle of 90° and having an angular half-width of between around 10° and around 75°. This parameter relates broadly to a measurement of granularity. One main subclass of leukocytes is granulocytes, a category of cells that includes neutrophils, eosinophils, and basophils, and is characterized by the presence of cytoplasmic granules. A portion of the granules in eosinophils displays a crystalline arrangement, leading to an increased DSS signal.

As used herein, the term "trigger" means the minimum electrical voltage that an electrical signal must exceed to be considered valid.

As used herein, the term "erythroblast" means any of the nucleated cells in bone marrow that develop into erythrocytes. As used herein, the term "erythrocyte" means the reddish, non-nucleated, disk-shaped blood cell that contains hemoglobin and is responsible for the color of blood.

One or more detectors are preferably placed in the paths of light emanating from the flow cell for measuring ALL, SAS, and IAS, or a subset of ALL, SAS, and IAS, or ALL and a detector measuring the combined ranges of SAS and IAS; as well as PSS and DSS. ALL-measuring subsystems collect light transmitted in the main beam of laser illumination, while scatter-measuring subsystems collect light outside the main beam. In ALL-measuring subsystems, the signal of interest is a negative signal subtracted from the steady-state laser signal, whereas in scatter-measuring subsystems (including SAS, IAS, PSS, and DSS), the signal is a small positive signal imposed on a very low background light level. IAS collection is similar to SAS collection, except the light is scattered at larger angles from the incident laser beam. In a preferred embodiment, ALL is collected by a detector having an angular half-width about 0.3° horizontally and about 1.2° vertically (measured from the optical axis of the system), and IAS is collected by a detector subtending angles between about 2° and about 10° from the laser axis.

As used herein, the expression "Open Mode" means a method of presenting the sample in an open tube to the automated instrument by a human operator. As used herein, the expression "Closed Mode" means a method of presenting the sample in a capped tube to the automated instrument by a robotic mechanism.

As used herein, the expression "measuring cells" refers to enumerating cells by means of optical measurement techniques to determine, e.g., size, refractive index, complexity, lobularity, granularity, and fluorescence when the cells are stained with a particular dye or fluorochrome.

The symbol "(s)" following the name of an object indicates that either the object alone or a plurality of the objects is being referred to, depending upon the context of the statement surrounding the mention of the object or objects.

As used herein, the term "leukocyte" means white blood cell. Unlike red blood cells, white blood cells occur in many different types. Examples of leukocytes include granulocytes (further subdivided into, e.g., neutrophils, eosinophils, and basophils), lymphocytes, and monocytes. The expression "reference method" means a method of the prior art against which a test method is compared.

The term "sickle cell" means a red blood cell shaped like a sickle. A sickle cell is typically resistant to a lytic reagent.

The term "thalassemic" relates to a genetic blood disorder in which the bone marrow cannot form sufficient red cells and red cell survival is also reduced.

The term "lymphocyte" means a white blood cell that matures in lymph nodes, the spleen, and other lymphoid tissues, enters the blood, and circulates throughout the body.

The expressions "nucleated red blood cell" and "erythroblast" mean an immature red blood cell that still contains a nucleus.

As used herein, the term "noise" includes, but is not limited to, such substances as lysed red blood cells in particulate form, cell debris, and platelet clumps.

As used herein, the term "event" means a particle generating a signal sufficient to trigger one or more detector, e.g., the IAS detector, whereby that detector signals the analyzer to collect measurements of that particle on all the detectors enabled on the analyzer, e.g., ALL, IAS, PSS, and DSS. Particles include, but are not limited to, are white blood cells (WBC), red blood cells (RBC), RBC fragments, platelets (PLT), lipids, and platelet clumps.

As used herein, the terms and phrases "diluent", "sheath", "sheath diluent", "diluent/sheath", and the like, mean a reagent used as diluent and as sheath fluid of the type suitable for use with hematology analyzers such as the CELL-DYN® Sapphire®, CELL-DYN® Ruby®, CELL-DYN® 3000 series, and CELL-DYN® 4000 series hematology analyzers, which reagents are commercially available from a variety of sources, including Abbott Laboratories, Santa Clara, Calif.

In certain cases, a hematology analyzer may include a source of light, a lens or system of lenses, a flow cell, and appropriate detectors, which components and functions thereof in a flow cytometry system are well-known to those of ordinary skill in the art. See, for example, U.S. Pat. Nos. 5,017,497; 5,138,181; 5,350,695; 5,812,419; 5,939,326; 6,579,685; 6,618,143; and U.S. Patent Publication Nos. 2003/0143117, US20080153170, US20080158561 and US20080268494, where exemplary sources of light, lenses, flow cells, and detectors are described in greater detail. All of the aforementioned references are incorporated herein by reference. Lasers, lenses, flow cells, and detectors suitable for use in this invention are commercially available from a variety of manufacturers, including Abbott Laboratories, Santa Clara, Calif.

Certain embodiments of the method described herein involve an automated method for simultaneous analysis of white blood cells, white blood cell differential (which identifies the proportion of neutrophils, eosinophils, basophils, lymphocytes and monocytes in the sample, and optionally of additional types of immature white blood cells, such as, e.g., immature granulocytes, blast cells, banded neutrophils, and variant lymphocytes), erythroblasts, reticulocytes, red blood cells, and platelets in liquid, such as, for example, blood. Other biological fluids, such as, for example, cerebrospinal fluid, ascites fluid, pleural fluid, peritoneal fluid, pericardial fluid, synovial fluid, dialysate fluid, and drainage fluid, can be used to determine various parameters of these fluids.

The optical subassembly of an exemplary hematology analyzer is schematically illustrated in FIG. 1. One of ordinary skill in the art would recognize that the choice, number and design of the components (e.g., the type of laser used, the number and specifications of the optical components, etc.) can vary greatly between analyzers and, as such, the hematology analyzer of FIG. 1 is provided as an example and should not be used to limit this disclosure. For example, in certain cases a hematology analyzer may or may not detect fluorescence.

Referring now to FIG. 1, in one embodiment, an apparatus 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scattering lens 30, a bulls-eye detector 32, a first photomultiplier tube 34, a second photomultiplier tube 36, and a third photomultiplier tube 38. The bullseye detector 32 has an inner detector 32a for ALL detection and an outer detector 32b for IAS detection.

In the discussion that follows, the source of light can be a laser. However, other sources of light can be used, such as, for example, lamps (e.g., mercury, xenon), light-emitting diodes (LEDs), and high-brightness LEDs. The light source can emit a beam of light at a wavelength in the range of from about 400 nm to about 450 nm, e.g., in the range of from about 400 nm to about 430 nm. For example, a laser that emits light at a wavelength of about 405 nm or 413 nm can be employed. In one embodiment, the source of light 12 can be a vertically polarized 405-nm diode Cube laser, commercially available from Coherent, Inc., Santa Clara, Calif. Operating conditions for the laser can be substantially similar to those of lasers currently used with automated hematology analyzers.

Additional details relating to an exemplary flow cell, exemplary lenses, an exemplary focusing lens, an exemplary fine-beam adjust mechanism, and an exemplary laser focusing lens can be found in U.S. Pat. No. 5,631,165, incorporated herein by reference, particularly at column 41, line 32 through column 43, line 11. The exemplary forward optical path system shown in FIG. 1 includes a spherical planoconvex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting ALL and IAS. U.S. Pat. No. 5,631,165 describes various alternatives to this detector at column 43, lines 12-52.

In this example, the first photomultiplier tube 34 (PMT1) measures DSS. The second photomultiplier tube 36 (PMT2) measures PSS, and the third photomultiplier tube 38 (PMT3) measures fluorescence in a range of wavelengths that is consistent with the emission spectrum of a fluorescent dye used, e.g., between around 450 nm and around 550 nm. Side-scattering and fluorescent emissions are directed to these photomultiplier tubes by dichroic beam splitter 40, which transmits and reflects efficiently at the required wavelengths to enable efficient detection, and beam splitter 42 (optionally a polarizing beam splitter). U.S. Pat. No. 5,631,165 describes various additional details relating to exemplary photomultiplier tubes at column 43, line 53 though column 44, line 4.

In particular cases and as would be readily apparent, the filters used in the fluorescence detection system (such as, e.g., filter 56 in front of photomultiplier 38) can filter out the light produced by the laser, thereby permitting only fluorescent light to reach the photomultiplier. In one embodiment, a fluorescence filter suitable for use with a laser having a wavelength of 405 nm is used.

In certain cases, sensitivity can be enhanced at photomultiplier tubes 34, 36, and 38 by using an immersion collection system. The immersion collection system is one that optically couples the first lens of optical condenser subsystem 44 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens subsystem with aberration correction sufficient for diffraction limited imaging used in high resolution microscopy. U.S. Pat. No. 5,631,165 describes various additional details of this optical system at column 44, lines 32-60.

The functions of other components shown in FIG. 1, i.e., a slit 46, a field lens 48, and a second slit 50, are described in U.S. Pat. No. 5,631,165, at column 44, line 63 through column 45, line 15. Photomultiplier tubes 34 and 36 detect side scattering (light scattered in a cone whose axis is approximately perpendicular to the incident laser beam), while photomultiplier tube 38 detects fluorescence (light emitted from the cells at a different wavelength from that of the incident laser beam).

For most measurements, the only reagent used is a sheath diluent. The sheath diluent used need be no different than that used on current hematology analyzers, e.g., the CELL-DYN® 3000 series and the CELL-DYN® 4000 series of hematology analyzers, although a different formulation can also be employed if desired. The sheath diluent can include as a reagent component a surfactant used to produce sphericity in the red blood cells in the sample.

In order to detect reticulocytes and nucleated red blood cells (NRBC), a nucleic acid dye can be employed. Fluorescent nucleic acid dyes suitable for use in the method described herein include, but are not limited to, a cell-permeable cyanine nucleic-acid stain that emits blue/violet light such as SYTO 40, SYTO 41, SYTO 42, SYTO 43, SYTO 44 and SYTO 45, (see, e.g., Wlodkowic (2008), *Cytometry A* 73, 496-507), both of which are commercially available from Life Technologies, as well as other cell-permeable dyes with similar absorption and emission spectra as a SYTO dye, e.g., a dye that has an absorbance maximum in the range of about 425 to about 440 nm (e.g., in the range of about 428 nm to about 435 nm) and an emission maximum in the range of about 450 nm to about 465 nm (e.g., in the range of about 452 nm to 463 nm), although dyes having emission/absorbtion maxima outside of these ranges may be employed in certain cases. Such dyes are collectively called "SYTO" dyes herein. Nucleic acid dyes that can be employed in the subject method may absorb light at the wavelength of the laser used, and emit light at a wavelength that is different from that of the wavelength of the laser, thereby allowing fluorescence to be detected. In one embodiment, the nucleic-acid dye binds to both RNA and DNA in the sample. In an alternative embodiment, two separate nucleic-acid dyes are employed, one of them binding preferentially to RNA and the other binding preferentially to DNA. In a preferred embodiment, the one or more nucleic acid dye employed in the method displays fluorescence enhancement upon binding, in order to reduce fluorescence background and improve the signal-to-noise ratio.

With use of a laser having a wavelength in the range of from about 400 nm to about 450 nm, red blood cells can be distinguished from white blood cells by a trigger value in forward scattering (IAS). A low IAS trigger value identifies platelets and red blood cells, thereby allowing those cells to be counted. A high IAS trigger value identifies white blood cells, thereby allowing white blood cells to be counted and red blood cells and platelets to be automatically rejected, and permitting a white blood cell differential. The low trigger value may in certain cases be 0.1 V. However, that value is dependent on factors such as the range of angles collected by the IAS detector, the efficiency of light collection, the quantum efficiency of the photodiode that is being used as the IAS (intermediate angle scatter) detector, the gain of the photodiode, the gain of any preamplifiers and amplifiers used, and, as such, the trigger value can be in the range of 0.005V to 10V, e.g., 2.3 V, depending on these factors.

The measurement process begins as the cell stream, having been diluted with the sheath diluent and being injected at such a rate that measurement of red blood cells incurs in a satisfactorily low level of coincidences, passes through the flow cell 28 in a laminar flowing sample stream surrounded by a sheath solution. The illuminated volume is bounded in the two directions normal to the flow axis by the hydrodynamically focused cell stream, and in the dimension parallel to the flow axis by the vertical beam waist of the laser beam, which is about 17 micrometers. The flow rate of the diluted sample in the sample stream is about 0.5 microliters per second for the red blood cell and platelet assay, and about 5 microliters per second for the white blood cell assay.

Figure 2:
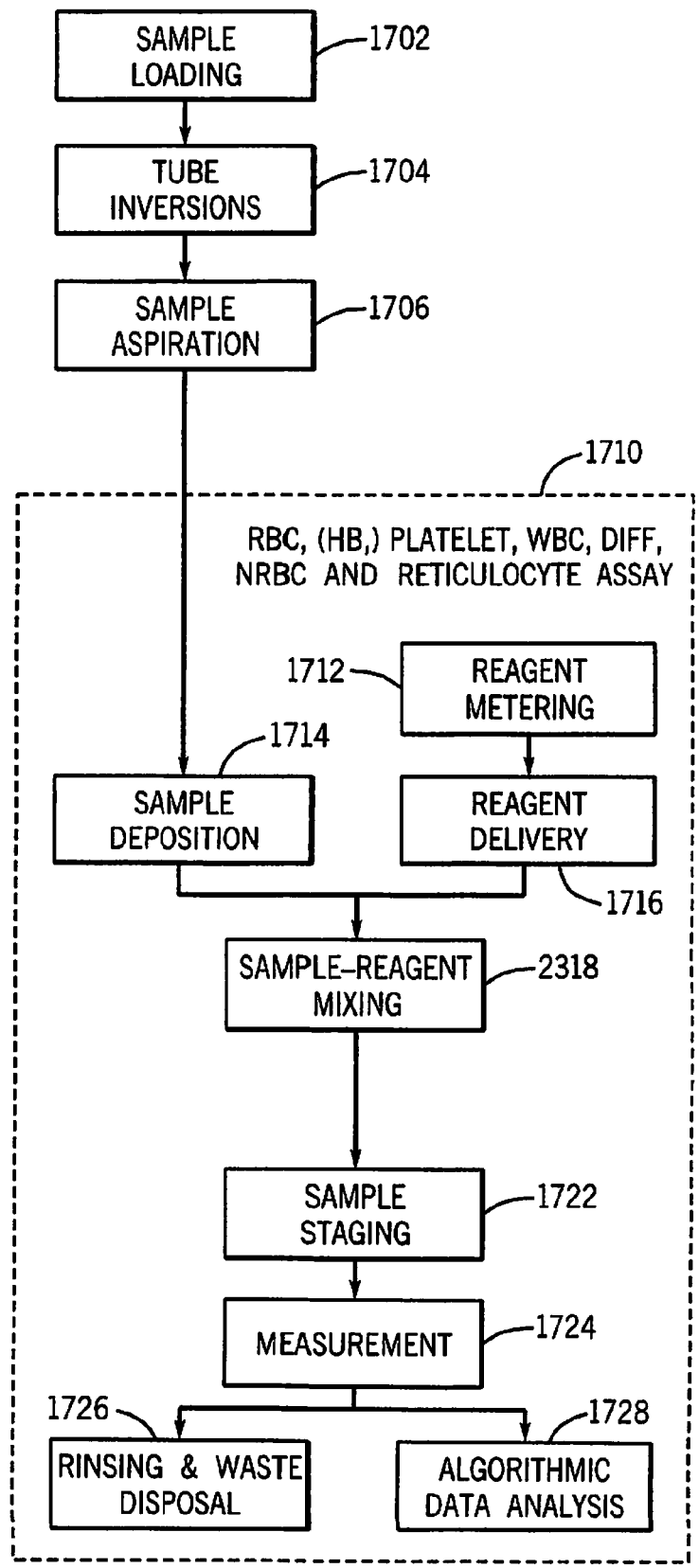
FIG. 2 is a flow chart illustrating the reduction in subsystems and the reduction in overall complexity attendant with the introduction of a single-dilution analyzer that does not require a lysing agent.

FIG. 2 shows an example of the subject method. Referring to FIG. 2, the initial stages of the sample preparation can be similar to those of the prior art, with the analogous steps of sample loading (1702), sample homogenization (1704), and sample aspiration (1706). In comparison to the prior art, the step of providing aliquots of the sample can be eliminated, because a single volume of the sample is used for processing. The three or more separate assays of the prior art can be combined into a single assay (1710), which yields those parameters that in the prior art require an assay for red blood cell and platelet parameters, an assay for white blood cells, white blood cell differential, and nucleated red blood cell parameters, an assay for quantification of reticulocyte parameters, and an assay for quantification of parameters related to hemoglobin. The volume of sample is delivered to a single container (1714), and the diluent solution is metered (1712)

and delivered to the same container (1716). In one embodiment, the ratio of diluent/sheath reagent to blood is about 100:1. The resulting mixture is homogenized (2318); the resulting mixture is then incubated for a length of time dependent on the nature of the reagent (e.g., whether one or more nucleic-acid dyes are employed) and on the types of assays desired to be performed on the blood sample (e.g., whether a reticulocyte assay, an erythroblast assay, or both assays are performed in addition to the standard CBC). The mixture of the sample and the reagent solution is then staged (1722) and immediately passed through the flow cell, where the flow cytometer measurements take place (1724). There are no separate sample mixtures to be processed sequentially; therefore, the sample is directed to waste and the flow cell rinsed (1726), thereby allowing another sample to follow immediately. For the measurement of the white blood cell differential, a rate of sample injection into the flow cell higher than the rate used for the count of red blood cells and platelets is used.

The signals from the flow cell measurements are processed and analyzed by the algorithm(s) (1728). The algorithms of the system can differentiate each cell population based on the optical signal intensities recorded for each cell on each detector channel, and the location and pattern of each cluster of cells in cytograms constructed from combinations of two or more of the optical measurements, or in histograms constructed from projections of the optical measurements along a chosen axis.

In particular embodiments, a universal clustering algorithm for analyzing the data can be used. Such an algorithm can perform satisfactorily with any kind of data. Such a universal clustering algorithm is described below.

A universal clustering algorithm can create groups of similar events (clusters) in a high-dimensional space (larger than 2). The algorithm can function with any reagent on any automated hematology analyzer. This is the first step of a data-driven algorithm. Algorithms of the prior art are knowledge-driven, i.e., what is being sought is known to some extent, and the data are categorized accordingly. Knowledge-driven algorithms can provide unusual results if the data are not as expected. Because in knowledge-driven algorithms assumptions are made about the data, data sets that fall outside the set defined by those assumptions may not be analyzed correctly.

Data-driven algorithms can function with any data, even data that contain unexpected events. Such algorithms can always provide the main clusters. Based on the output of this type of algorithm, the kind of data being observed can be determined, and then an appropriate algorithm (including knowledge-based algorithms) for the detailed analysis can be used. A clustering algorithm allows a coarse classification of data type (based on few, if any, broad assumptions) before a second algorithm executes a detailed classification based on more stringent assumptions.

In what follows, one embodiment of a clustering algorithm approach is described. A k-means clustering routine is used to obtain an initial set of about 10 clusters. The number 10 is chosen to be higher than the number of meaningful clusters that are expeted to be present in the data sets to be analyzed. After the k-means routine returns, the clusters are merged, based on some measure of their distance. A fixed distance threshold value can be used, and when the distance between two clusters is below that value, those clusters can be merged. Merging continues until there are no more pairs of clusters remaining that are closer to each other than the cut-off value. Unlike the k-means routine, the clustering routine described herein returns a variable number of clusters.

The distance measure described herein is a combination of cluster locations and cluster spreads.

In certain cases, the data is clustered by the k-means method, which aims to partition the points into k groups such that the sum of squares from points to the assigned cluster centers is minimized. At the minimum, all cluster centers are at the mean of their Voronoi sets (the set of data points which are nearest to the cluster center).

The algorithm of Hartigan and Wong (Hartigan, J. A., and Wong, M. A. (1979), "Algorithm AS 136: A K-means clustering algorithm," *Journal of the Royal Statistical Society, Series C (Applied Statistics)* 28, 100-108) can be used by default. In certain cases a specific algorithm can be employed, such as those described by MacQueen (MacQueen, J. (1967), "Some methods for classification and analysis of multivariate observations," in *Proceedings of the Fifth Berkeley Symposium on Mathematical Statistics and Probability*, eds L. M. Le Cam & J. Neyman, 1967 1, pp. 281-297. Berkeley, Calif.: University of California Press), Lloyd (Lloyd, S. P. (1957), "Least squares quantization in PCM," Technical Note, Bell Laboratories. Published in 1982 in *IEEE Transactions on Information Theory* 28, 128-137) and Forgy (Forgy, E. W. (1965), "Cluster analysis of multivariate data: efficiency vs. interpretability of classifications," *Biometrics* 21, 768-769). The Hartigan-Wong algorithm can also be employed, but trying several random starts is often recommended. Except for the Lloyd-Forgy method, k clusters will always be returned if a number is specified. If an initial matrix of centers is supplied, it is possible that no point will be closest to one or more centers, which is currently an error for the Hartigan-Wong method. The foregoing publications are incorporated herein by reference.

The clustering algorithm used need not require any assumptions about the data. The clustering algorithm used can return an adequate summary of the main components of the data observed. From the data observed, assumptions can be made about the kind of a sample being observed. Detailed algorithms that are tailored to the different samples encountered can then be employed.

With a clustering approach as the first step in the classification algorithm, a very good rough classification of the sample can be obtained, and then an appropriate detailed algorithm can be run. A second advantage of clustering algorithms is that they can more accurately locate small populations, such as, for example, immature granulocytes.

Certain embodiments of the method described herein have advantages. In certain cases, no lysing agent is required, thereby increasing the accuracy of the count of white blood cells. Further, in certain cases, no lysing step is required, thereby increasing the throughput of the analyzer. A strong hemoglobin signal allows the measurement of the hemoglobin concentration in red blood cells on a cell-by-cell basis as they pass through the flow cell for enumeration. Furthermore, in certain cases, the method only requires a single dilution of the blood sample, thereby simplifying the fluidics of the hematology analyzer.

Certain embodiments of the apparatus and method described herein provide a significant reduction in the complexity of the analyzer, in the number of separate processing steps required for a standard complete blood count, in the number and amount of reagents used to obtain a complete blood count, in the cost of its manufacture, in the risk of failure during operation, and in the cost of maintenance and service. Furthermore, the apparatus and method described herein can eliminate the need to lyse red blood cells during the white blood cell assay, thereby eliminating the interference with the white blood cell count or differential assay from lyse-resistant red blood cells (including, e.g., sickle cells, target cells, and erythroblasts from neonates).

In one embodiment, the red blood cell lysis incubation step is not performed and, in certain embodiments, the multiple assays of a conventional method are combined into a single assay. For example, each of the two or more delivery subsystems of the lysing procedure of the prior art that is eliminated by adoption of the single dilution procedure of the present invention may include the following components: (a) a precision metering syringe; (b) a syringe assembly; (c) a syringe stepper motor; (d) a stepper motor driver board; (e) several lengths of noncompliant tubing; (f) several pinch valves; (g) the corresponding pilot valves that operate the pinch valves, or alternatively the solenoids operating the pinch valves; (h) the electronic board components driving the pilot valves or the solenoids; (i) a container used to mix one aliquot of sample with the metered quantity of reagent; (j) a motor used to mix the sample aliquot with the reagent solution; (k) the mixer motor driver board; (l) the firmware for controlling the stepper motor, the mixer motor, and the several pilot valves or solenoids; (m) the power source(s) for the stepper motor, the mixer motor, and the pilot valves or solenoids; (n) the fans for removing the heat from the flow panel due to operation of the pilot valves or solenoids. Taking as example the CELL-DYN® Sapphire® hematology analyzer, where three reagent delivery subsystems supporting flow cytometry measurements are currently in use (that for the red blood cell/platelet assay; that for the white blood cell, white blood cell differential, and nucleated red blood cell assay; and that for the optional reticulocyte assay), adoption of the apparatus and method described herein would reduce these to a single reagent delivery subsystem. Subsystems supporting impedance measurements (for cell volume determination) or colorimetric measurements (for bulk hemoglobin determination) need not be affected. However, these subsystems, too, could optionally be eliminated altogether for additional benefits in simplicity, reliability, and cost, because the apparatus and method used for a lysis-free single-dilution approach could provide all of the reportable parameters (including mean cell volume and overall hemoglobin concentration) that are required of a commercial hematology analyzer.

The reagents used in the analyzer can be reduced relative to the set in the prior art (which includes a lysing agent for use in the white blood cell assay, an optional nucleic acid dye added to the lysing agent for use in the concurrent nucleated red blood cell assay, a diluent solution containing optional sphering reagent for the red blood cell/platelet assay, a reagent solution used for the reticulocyte assay, which reagent solution includes a nucleic acid dye, and a strong lysing agent used for hemoglobin quantification) to a single reagent solution, which comprises a diluent, typically a saline diluent. The single reagent solution preferably comprises an isovolumetric sphering reagent, such as, e.g., a surfactant, acting on the membrane of the red blood cells to confer upon them an approximately spherical form while leaving their volume substantially unchanged, in order to prevent orientation-dependent light scattering results from otherwise essentially equivalent cells. The single reagent solution optionally comprises one or two nucleic acid dyes for reticulocyte and nucleated red blood cell analysis. At least one of the nucleic acid dyes should be capable of staining RNA, and at least one of the nucleic acid dyes should be capable of staining DNA. Alternatively, the at least one nucleic acid can be capable of staining both RNA and DNA. Another optional ingredient of the reagent solution for use in the method described herein is a selective permeabilizing agent. Only one dilution ratio is used. The cell counting and identification algorithms are combined from a set dedicated to each of the currently employed assays to a single set to be applied to the single assay being performed. Furthermore, the algorithms employ similar data (signals) to those that are currently employed. The precision of results can be automatically maintained by design. The coincidence levels can be maintained by design.

The method described above can be employed to measure the number of individual red blood cells, the volume of individual red blood cells, and the amount of hemoglobin in individual red blood cells of a sample, thereby permitting the analysis of further characteristics of the population. In one embodiment, the method can further comprise calculating the proportion (which can, for example, be expressed as a percentage, fraction or another number), of red blood cells having a defined characteristic. For example, the method can be employed to calculate the proportion of red blood cells having a volume above and/or below a defined volume (e.g., the percentage of cells larger than 120 fL, i.e., the percentage of "macrocytic" red blood cells; or the percentage of cells smaller than 60 fL, i.e., the percentage of "microcytic" red blood cells). In another embodiment, the method can be employed to calculate the proportion of red blood cells having a hemoglobin concentration above and/or below a defined volume (e.g., the percentage of red blood cells having a cellular hemoglobin concentration of less then 28 g/dL, i.e., the percentage of "hypochromic" red blood cells; or the percentage of red blood cells having a cellular hemoglobin concentration of greater than 41 g/dL, i.e., the percentage of "hyperchromic" red blood cells). Likewise, the volumes and/or hemoglobin concentrations of individual red blood cells of a population can be statistically analyzed to identify other statistical measures that describe, for example, the shape of the distribution or variation of the volume or hemoglobin concentration of individual RBCs within the population. In one exemplary embodiment, the width of the distribution of hemoglobin concentration in the population of red blood cells is calculated.

In a further embodiment, the method can further involve identifying reticulocytes in the sample. Reticulocytes are a subset of red blood cells that are distinguishable from other red blood cells by, e.g., fluorescence. The method can also be used to further analyze the reticulocytes in a sample by, for example, calculating the mean amount of hemoglobin in the reticulocytes, the mean concentration of hemoglobin in the reticulocytes, or the mean volume of the reticulocytes. The method can further be employed to present the reticulocyte population in comparison to the mature red blood cell population on appropriate cytograms, e.g., on a cytogram displaying the volume vs. hemoglobin concentration of individual reticulocytes and red blood cells in the sample.

The hematology analyzer described above can be employed, for example, to investigate red blood cell disorders or anemias, and to make treatment decisions, if necessary. Examples of anemia include iron deficiency anemia, anemia of chronic disorder, and megaloblastic anemia caused by vitamin $B_{12}$ or folic acid. For example, administration of iron supplement is extremely effective as a treatment for iron deficiency anemia, but not for anemia of chronic disorder. The cause of the anemia is therefore important to the treatment of the anemia.

Iron deficiency is the most prevalent single deficiency state on a worldwide basis. It is important economically because it diminishes the capability of affected individuals to perform physical labor, and it diminishes both growth and learning in children.

Absolute iron deficiency, with anemia or without anemia, and functional iron deficiency are high-frequency clinical conditions, and patients with these conditions have iron-deficient erythropoiesis. Absolute iron deficiency is defined as a decrease in total body iron content. Iron-deficiency anemia occurs when iron deficiency is sufficiently severe to diminish erythropoiesis and cause the development of anemia. Functional iron deficiency describes a state where the total iron content of the body is normal or even elevated, but the iron is "locked away" and unavailable for the production of red blood cells. This condition is observed mainly in patients with chronic renal failure who are on hemodialysis, and in patients with chronic inflammation or chronic infections.

Iron status can be measured using hematological and biochemical indices. Each parameter of iron status reflects changes in different forms of body iron storage and is affected at different levels of iron depletion. Specific iron measurements include hemoglobin, mean cell volume, hematocrit, erythrocyte protoporphyrin, plasma iron, transferrin, transferrin saturation levels, serum ferritin, soluble transferrin receptors, and red-cell distribution width.

Hemoglobin has been used longer than any other iron status parameter. It provides a quantitative measure of the severity of iron deficiency once anemia has developed. Hemoglobin determination is a convenient and simple screening method and is especially useful when the prevalence of iron deficiency is high, as in pregnancy or infancy. The limitations of using hemoglobin as a measure of iron status are its lack of specificity (since factors such as vitamin $B_{12}$ or folate deficiency, genetic disorders and chronic infections can limit erythropoiesis) and its relative insensitivity due to the marked overlap in values between normal and iron-deficient populations. To identify iron-deficiency anemia, hemoglobin is measured together with more selective measurements of iron status.

A reduction in mean cell volume occurs when iron deficiency becomes severe, at about the same time that anemia starts to develop. It is a fairly specific indicator of iron deficiency once thalassemia and the anemia of chronic disease have been excluded. A cut-off value of 80 fl is accepted as the lower limit of the normal range in adults. The red-cell distribution width (RDW) has been used recently in combination with other parameters for the classification of anemias. RDW reflects the variation in the size of the red cells and can be used to detect subtle degrees of anisocytosis.

The most commonly used iron status parameters at present are transferrin saturation (TSAT) and serum ferritin. However, both are indirect measures of iron status. Transferrin is a transport protein that contains two iron binding sites by which it transports iron from storage sites to erythroid precursors. TSAT (i.e., the percentage of total binding sites that are occupied by iron) is a measure of iron that is available for erythropoiesis. TSAT is calculated by dividing the serum iron by the total iron binding capacity, a measurement of circulating transferrin, and multiplying by 100. Ferritin is a storage protein that is contained primarily within the reticuloendothelial system, with some amounts released in the serum. Under conditions of iron excess, ferritin production increases to offset the increase in plasma iron. The level of ferritin in the serum, therefore, reflects the amount of iron in storage.

Reticulocytes are immature red blood cells with a maturation time of only 1 to 2 days before turning into mature red blood cells. When reticulocytes are first released from the bone marrow, measurement of their hemoglobin content can provide the amount of iron immediately available for erythropoiesis. A less-than-normal hemoglobin content in these reticulocytes is an indication of inadequate iron supply relative to demand. The amount of hemoglobin in these reticulocytes also corresponds to the amount of hemoglobin in mature red blood cells. The hemoglobin content of reticulocytes has been evaluated recently in numerous studies as a test for absolute iron deficiency and functional iron deficiency and has been found to be highly sensitive and specific. However, exact threshold values have not been established, because the threshold values vary depending on the laboratory and instrument used.

Erythropoietin is effective in stimulating production of red blood cells, but without an adequate iron supply to bind to hemoglobin, the red blood cells will be hypochromic, i.e., low in hemoglobin content. Thus, in states of iron deficiency, a significant percentage of red blood cells leaving the bone marrow will have low hemoglobin content. By measuring the percentage of red blood cells with hemoglobin content less than 28 g/dL, iron deficiency can be detected. A percentage of hypochromic cells greater than 10% has been correlated with iron deficiency, and hence has been used as a diagnostic criterion for detection of iron deficiency.

In addition to providing a white blood cell count, the above-described apparatus and method can provide a white blood cell differential that provides the percentage of each type of white blood cell (WBC) in a blood sample, thereby revealing if there are certain pathologies likely affecting the white blood cells in the sample. Neutrophils can increase in response to bacterial infection or inflammatory disease. Severe elevations in neutrophils may be caused by various bone marrow disorders, such as chronic myelogenous leukemia. Decreased neutrophil levels may be the result of severe infection or other conditions, such as responses to various medications, particularly chemotherapy. Eosinophils can increase in response to allergic disorders, inflammation of the skin, and parasitic infections. They can also increase in response to some infections or to various bone marrow disorders. Decreased levels of eosinophils can occur as a result of infection. Basophils can increase in cases of leukemia, chronic inflammation, the presence of a hypersensitivity reaction to food, or radiation therapy. Lymphocytes can increase in cases of viral infection, leukemia, cancer of the bone marrow, or radiation therapy. Decreased lymphocyte levels can indicate diseases that affect the immune system, such as lupus, and the later stages of HIV infection. Monocyte levels can increase in response to infection of all kinds as well as to inflammatory disorders. Monocyte counts are also increased in certain malignant disorders, including leukemia. Decreased monocyte levels can indicate bone marrow injury or failure and some forms of leukemia. Since percentages might be misleading in some patients, absolute values of the various types of WBCs can also be reported, such as the absolute neutrophil count (ANC). Absolute values are calculated by multiplying the number of WBCs by the percentage of each type of white cell and can aid in diagnosing illness and monitoring therapy.

In one embodiment, a physical memory containing instructions (i.e. "programming") for performing the method described herein is provided. In some embodiments, the memory can comprise a physical computer-readable medium comprising: i. programming to differentiate and count white blood cells in a sample using multiple in-flow optical measurements obtained from a first portion of the sample that has been introduced into a flow cell at a high rate and ii. programming to differentiate and count red blood cells and platelets in the sample using multiple in-flow optical measurements obtained from a second portion of the sample that has been introduced into a flow cell at a low rate. In one embodiment, data from the hematology analyzer is collected, and programming containing an algorithm for the calculation is executed, using the multiple in-flow optical measurements as inputs.

The programming can be provided in a physical storage or transmission medium. A computer receiving the instructions can then execute the algorithm and/or process data obtained from the subject method. Examples of storage media that are computer-readable include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network.

The method described herein can be automatically executed each time a sample is run, or each can be executed on a sample in response to different test selections by an operator.

The following non-limiting examples illustrate the method of this invention. In the following examples, the parameters that are measured are described as follows:

(1) size, or 0° channel: this detection channel measures two different quantities, depending on the analyzer platform:
  (a) ALL: extinction, i.e., light lost from the main beam (e.g., on the CELL-DYN® Sapphire); or
  (b) SAS: light scattered at angles ranging from about 1° to about 3° with respect to the laser beam propagation axis (e.g., on the CELL-DYN® Ruby®)
(2) IAS, complexity, 7° or 10° channel: light scattered at angles ranging from about 3° to about 10° with respect to the laser beam propagation axis.
(3) PSS, lobularity, or 90° channel: light scattered orthogonally to the laser beam which maintains vertical polarization.
(4) DSS, granularity, or 90° depolarized channel: light scattered orthogonally to the laser beam, which by interaction with cellular subcomponents has acquired horizontal polarization.

EXAMPLE 1

Figure 3:
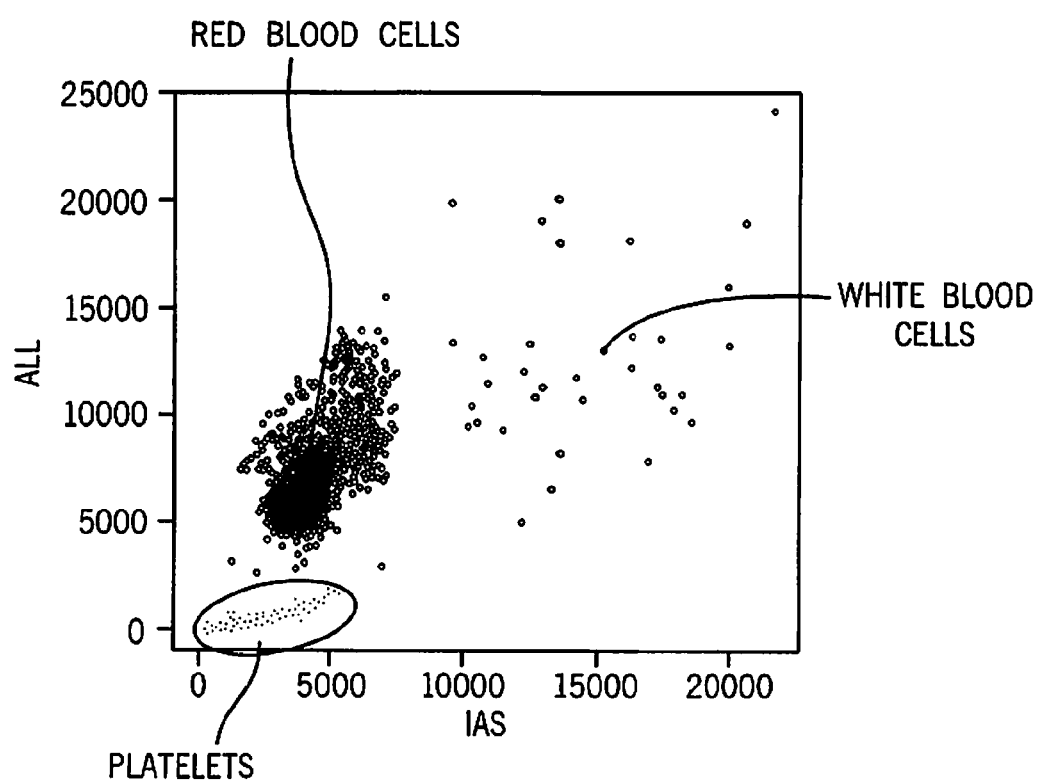
FIG. 3 is a cytogram of unlysed whole blood, wherein the wavelength of the light source was 405 nm. It can be seen that there is clear separation between platelets, red blood cells, and white blood cells. The number of white blood cells counted is too low, compared to the other populations, to allow a white blood cell differential to be performed. In order to increase the proportion of white blood cell events that are collected, an intermediate angle scattering (IAS) trigger threshold value corresponding to about 8000 on the IAS axis of the cytogram is required.

This example illustrates separation of red blood cells, white blood cells, and platelets in a sample of unlysed whole blood carried out on a prototype analyzer that uses a laser having a wavelength of 405 nm. The results are shown in FIG. 3. It can be seen that there is clear separation between platelets, red blood cells, and white blood cells. The number of white blood cells is too low to see a white blood cell differential. In order to collect more white blood cell events, an IAS trigger value corresponding to about 8000 on the IAS is required.

EXAMPLE 2

Figure 4:
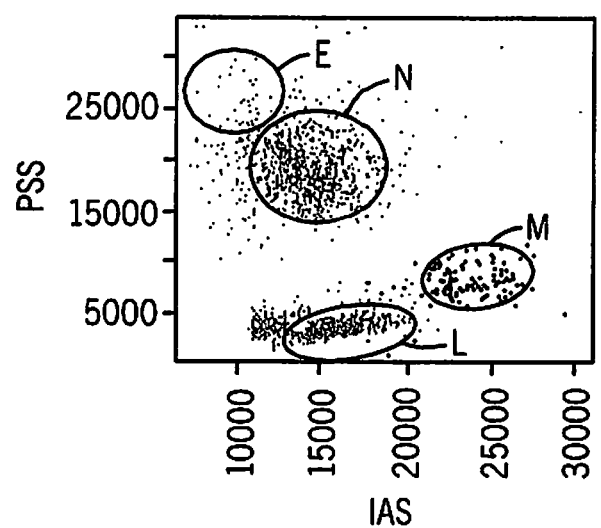
FIG. 4 is a cytogram of the white blood cells of an unlysed clinical blood sample with a high rate of sample introduction (injection) and an intermediate angle scattering (IAS) trigger threshold at channel 7000. The white blood cell differential is shown, with monocytes in the area designated by the letter "M", lymphocytes in the area designated by the letter "L", neutrophils in the area designated by the letter "N", and eosinophils in the area designated by the letter "E." The classification is achieved without a clustering algorithm.
Figure 5A:
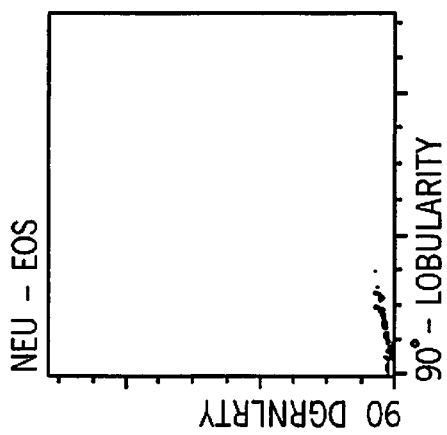
FIGS. 5A, 5B, 5C, and 5D are cytograms of the prior art illustrating a sample with lysis-resistant RBCs interfering with the WBC and lymphocyte counts, presenting a lymphocyte percentage of 95%. The cytograms were generated by a CELL-DYN® Sapphire® hematology analyzer using a conventional lysing agent of low lytic strength. The wavelength of the laser, 488 nm, was not in the range described herein (i.e., 400 nm to 450 nm).
Figure 5B:
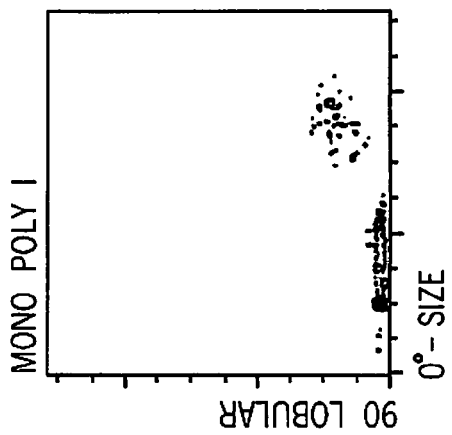
Figure 5C:
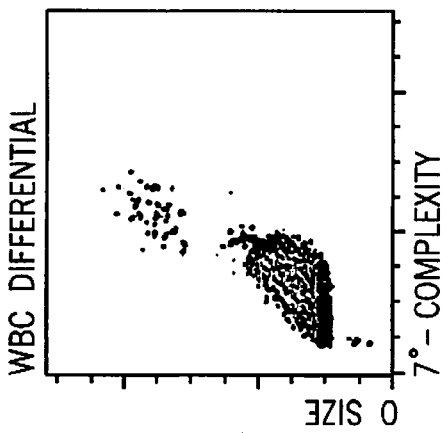
Figure 5D:
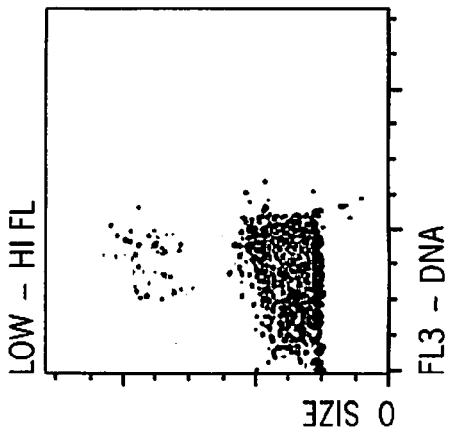
Figure 7A:
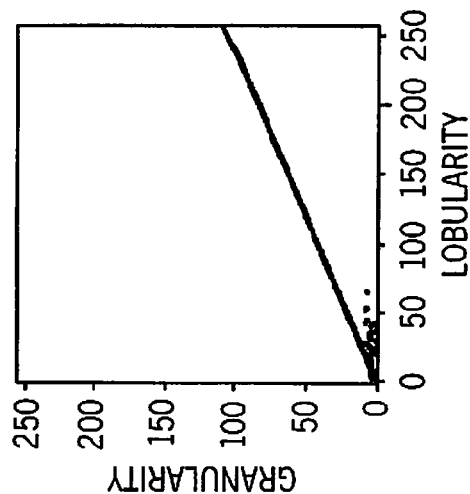
FIGS. 7A, 7B, 7C, and 7D are cytograms illustrating the same sample as in FIGS. 5A, 5B, 5C, and 5D and presenting a lymphocyte percentage of 55%. The cytograms were generated by a CELL-DYN® Ruby® hematology analyzer using a conventional lysing agent of an intermediate lytic strength. The wavelength of the laser, 633 nm, was not in the range described herein (i.e., 400 nm to 450 nm).
Figure 7B:
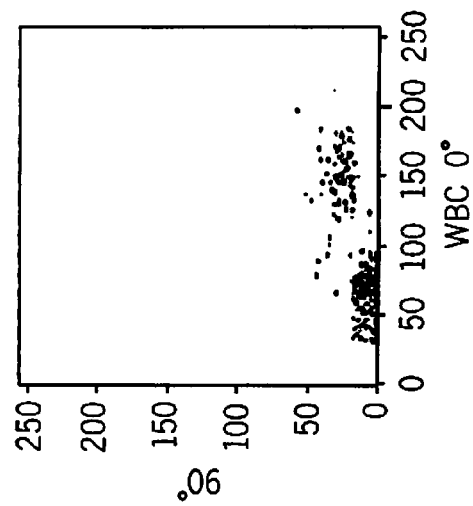
Figure 7C:
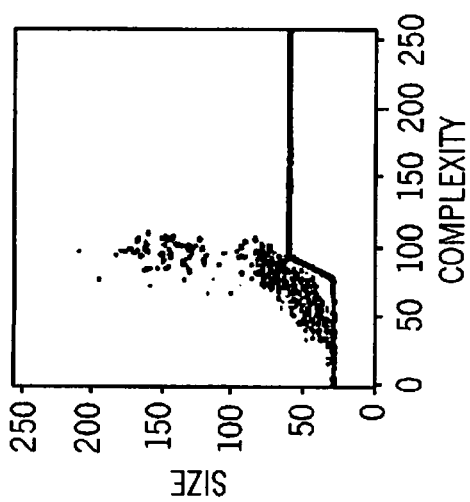
Figure 7D:
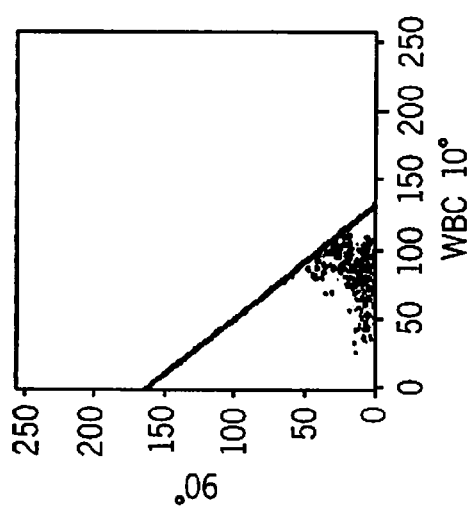

This example illustrates a white blood cell differential carried out on a prototype analyzer that uses a laser having a wavelength of 405 nm, wherein the method does not employ a lysing agent. The results are shown in FIG. 4, where monocytes are designated by the letter "M", lymphocytes are designated by the letter "L", neutrophils are designated by the letter "N", and eosinophils are designated by the letter "E." The classification is achieved without a clustering algorithm.

EXAMPLE 3

This example illustrates that issues encountered with lysis-resistant red blood cells interfering with the white blood cell count by the CELL-DYN® Ruby® hematology analyzer and the CELL-DYN® Sapphire® hematology analyzer are significantly improved with a laser having a wavelength of 405 nm. CELL-DYN® Ruby® hematology analyzers employ a wavelength of 633 nm. CELL-DYN® Sapphire® hematology analyzers employ a wavelength of 488 nm. The same blood sample was run on three different analyzers using four separate assays; the results are described below, with reference to FIGS. 5-8.

FIGS. 5A, 5B, 5C, and 5D show that the results generated by the analyzer would indicate that the sample has a lymphocyte percentage of 95%, as measured with a CELL-DYN® Sapphire° hematology analyzer employing a laser having a wavelength outside the range of 400 nm to 450 nm and a lysing agent of low lytic strength. FIGS. 6A, 6B, 6C, and 6D show that the results generated by the analyzer would indicate that the sample has a lymphocyte percentage of 48%, as measured with a CELL-DYN® Sapphire° hematology analyzer employing a laser having a wavelength outside the range of 400 nm to 450 nm and a lysing agent of high lytic strength. FIGS. 7A, 7B, 7C, and 7D show that the results generated by the analyzer would indicate that the sample has a lymphocyte percentage of 55%, as measured with a CELL-DYN® Ruby° hematology analyzer employing a laser having a wavelength outside the range of 400 nm to 450 nm and a lysing agent of intermediate strength.

Figure 8:
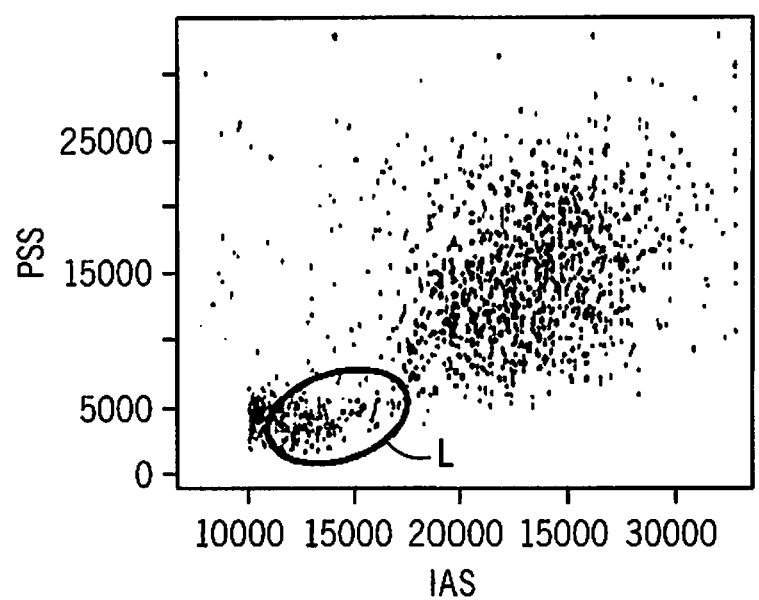
FIG. 8 is a cytogram illustrating the same sample as in FIGS. 5A, 5B, 5C, and 5D and presenting a lymphocyte percentage of 12%. The cytograms were generated by a prototype hematology analyzer using a 405-nm laser and the single-dilution techniques described herein without a lysing agent. Lymphocytes are in the area designated by the letter "L."

FIG. 8 indicates that the sample has a lymphocyte percentage of 12%, as measured with a prototype analyzer equipped with a 405 nm laser, but not employing a lysing agent and using the single dilution technique described herein. Here the lymphocyte percentage is measured to be 12%. The lymphocytes are designated by the letter "L." The reference method used to establish truth for this particular sample is a microscope slide review by a trained operator, which provided for this sample a lymphocyte percentage of 10%. The use of the 405 nm laser and the single dilution technique described herein provided results that were closest to those of the reference method, whereas both the CELL-DYN® Sapphire° hematology analyzer (for both assays with low lytic strength and high lytic strength) and the CELL-DYN® Ruby° hematology analyzer provided results that were significantly discrepant due to interference from lysis-resistant red blood cells. The data show that the hematology analyzer using a 405 nm laser is superior for reducing or eliminating interference from lysis-resistant red blood cells in the measurement of white blood cell count and in the white blood cell differential.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A hematology analyzer comprising:
  a) a flow cell through which a whole blood sample is introduced at both a first flow rate and a second flow rate that is different from the first flow rate;
  b) a laser having a wavelength in the range of from about 400 nm to about 450 nm for directing light to said flow cell;
  c) a plurality of detectors for detecting light scattering by cells on a plurality of in-flow optical measurement channels; and
  d) a data analysis workstation comprising a processor, wherein the processor comprises a non-transient, computer-readable medium programmed with instructions that, when executed by the processor, cause the hematology analyzer to:
    (i) introduce a first portion of the blood sample into the flow cell at the first flow rate and direct the laser to the flow cell to generate a plurality of first flow rate optical data using the plurality of detectors;

(ii) introduce a second portion of the same blood sample into the flow cell at the second flow rate and direct the laser to the flow cell to generate a plurality of second flow rate optical data using the plurality of detectors;

(iii) differentiate and count white blood cells in the blood sample using the first flow rate optical data and at least one algorithm to differentiate and count different types of white blood cells; and (iv) differentiate and count red blood cells and platelets in the blood sample using the second flow rate optical data.

2. The hematology analyzer of claim 1, wherein the plurality of detectors comprises one or more of: an axial light loss (ALL) detector, a small angle scattering (SAS) detector, an intermediate angle scattering (IAS) detector, a polarized side scattering (PSS) detector, a depolarized side scattering (DSS) detector, and a fluorescence detector.

3. The hematology analyzer of claim 1, wherein said plurality of detectors comprises a detector for obtaining light extinction measurements at an angle of from about 0° to about 1°.

4. The hematology analyzer of claim 1, wherein said plurality of detectors comprises a detector for obtaining light scattering measurements at an angle of from about 3° to about 10°.

5. The hematology analyzer of claim 1, wherein, in said analyzer, at least one in-flow optical measurement threshold is set to qualify all signals from white blood cells and discriminate all other signals.

6. The hematology analyzer of claim 1, wherein the non-transient, computer-readable medium further comprises instructions for estimating the concentration of hemoglobin in the blood sample using measurements of the concentration of hemoglobin in each individual red blood cell using a plurality of optical data generated from the plurality of detectors and measurements of red blood cell counts to determine the concentration of red blood cells in the blood sample.

7. The hematology analyzer of claim 1, wherein the non-transient, computer-readable medium further comprises instructions for performing a clustering algorithm for analyzing the optical data received at the data analysis workstation.

8. The hematology analyzer of claim 7, wherein the clustering algorithm includes a k-means clustering routine.

9. The hematology analyzer of claim 1, wherein the non-transient, computer-readable medium further comprises instructions for controlling the rate at which the blood sample is introduced into the flow cell.

10. The hematology analyzer of claim 9, wherein the first flow rate is up to about 5 microliters per second.

11. The hematology analyzer of claim 9, wherein the second flow rate is at least about 0.5 microliters per second.

12. The hematology analyzer of claim 9, wherein the first flow rate is about ten times greater than the second flow rate.

13. The hematology analyzer of claim 9, wherein the second flow rate introduces the blood sample into the flow cell at an injection rate ranging from about 50,000 up to about 300,000 red blood cells per second.

14. The hematology analyzer of claim 9, wherein the first flow rate introduces the blood sample into the flow cell at an injection rate ranging from about 0 up to about 50,000 white blood cells per second.

15. The hematology analyzer of claim 1, wherein the non-transient, computer-readable medium further comprises instructions for identifying red blood cell disorders selected from the group consisting of: iron deficiency anemia, anemia of chronic disorder, and megaloblastic anemia.

16. The hematology analyzer according to claim 1, wherein the laser has a wavelength ranging from about 400 nm to about 430 nm.

* * * * *